(12) United States Patent
Jones et al.

(10) Patent No.: US 10,851,335 B2
(45) Date of Patent: Dec. 1, 2020

(54) FLOW ASSEMBLY FOR CELLS

(71) Applicant: Indiana University Research and Technology Corporation, Indianapolis, IN (US)

(72) Inventors: Lisa M. Jones, Baltimore, MD (US); Aimee Rinas, Fishers, IN (US)

(73) Assignee: Indiana University Research and Technology Corporation, Bloomington, IN (US)

( * ) Notice: Subject to any disclaimer, the term of this patent is extended or adjusted under 35 U.S.C. 154(b) by 0 days.

(21) Appl. No.: 15/564,139

(22) PCT Filed: Mar. 31, 2016

(86) PCT No.: PCT/US2016/025188
§ 371 (c)(1),
(2) Date: Oct. 3, 2017

(87) PCT Pub. No.: WO2016/164244
PCT Pub. Date: Oct. 13, 2016

(65) Prior Publication Data
US 2018/0079998 A1  Mar. 22, 2018

Related U.S. Application Data

(60) Provisional application No. 62/144,542, filed on Apr. 8, 2015.

(51) Int. Cl.
| | |
|---|---|
| *C12M 3/06* | (2006.01) |
| *C12M 1/34* | (2006.01) |
| *C12M 1/26* | (2006.01) |
| *C12M 1/00* | (2006.01) |
| *G01N 33/487* | (2006.01) |
| *C01B 15/00* | (2006.01) |

(52) U.S. Cl.
CPC ............ *C12M 23/16* (2013.01); *C12M 29/00* (2013.01); *C12M 33/00* (2013.01); *C12M 41/46* (2013.01); *G01N 33/487* (2013.01); *C01B 15/00* (2013.01); *C12M 1/34* (2013.01)

(58) Field of Classification Search
CPC ...... C12M 23/16; C12M 41/46; C12M 29/00; C12M 33/00; C12M 1/34; G01N 33/487; C01B 15/00
USPC .......................................................... 435/29
See application file for complete search history.

(56) References Cited

U.S. PATENT DOCUMENTS

| | | |
|---|---|---|
| 6,177,266 B1 | 1/2001 | Krishnamurthy et al. |
| 2005/0134833 A1 | 6/2005 | Kramer |
| 2008/0067068 A1* | 3/2008 | Li ........................ B03C 5/005 |
| | | 204/451 |
| 2009/0042737 A1 | 2/2009 | Katz et al. |
| 2011/0096327 A1 | 4/2011 | Papautsky et al. |
| 2011/0207207 A1 | 8/2011 | Gibson et al. |
| 2015/0024476 A1 | 1/2015 | Butler et al. |

OTHER PUBLICATIONS

International Search Report and Written Opinion issued by the ISA/US, Commissioner for Patents, dated Jun. 20, 2016, for International Application No. PCT/US2016/025188; 7 pages.

International Preliminary Report on Patentability issued by the International Bureau of WIPO, Geneva, Switzerland, dated Oct. 10, 2017, for International Application No. PCT/US2016/025188; 6 pages.

* cited by examiner

*Primary Examiner* — Jennifer M. H. Tichy
(74) *Attorney, Agent, or Firm* — Faegre Drinker Biddle & Reath LLP

(57) ABSTRACT

In one embodiment, a flow assembly for cells comprises a first flow path configured to receive a plurality of cells, a second flow path configured to receive a buffer, and a third flow path configured to receive the plurality of cells and the buffer. The plurality of cells are in a single-file orientation and the buffer generally surrounds the single-file orientation of the plurality of cells when in the third flow path.

5 Claims, 6 Drawing Sheets

FLOW ASSEMBLY FOR CELLS

CROSS-REFERENCE TO RELATED APPLICATIONS

The present application is a U.S. National Stage Application of International Patent Application No. PCT/US2016/025188, filed Mar. 31, 2016, which claims the benefit of priority to U.S. Provisional Patent Application No. 62/144,542, filed Apr. 8, 2015, and entitled "FLOW ASSEMBLY FOR CELLS," the complete disclosures of which is are expressly incorporated by reference herein.

FIELD OF THE INVENTION

The present invention relates generally to an assembly configured for the flow of cells, and more particularly, to a micro-flow assembly configured for a single-file flow of cells.

BACKGROUND OF THE DISCLOSURE

In cell fast photochemical oxidation of proteins ("IC-FPOP") is a tool for characterizing protein structure within a cell. Through IC-FPOP, hydrogen peroxide is photolyzed using an excimer laser to form hydroxyl radicals. The hydroxyl radicals covalently label side chains of amino acids exposed to solvent, thereby allowing for oxidative characterization of the protein structure within a cell.

However, current flow systems used for in vitro analysis of the protein structure within a cell may not be effective with IC-FPOP. More particularly, current flow systems may lead to cell aggregation which may clog the flow system and/or lead to inconsistent labeling and characterization of the cells because not every cell is exposed to the laser equally.

SUMMARY OF THE DISCLOSURE

In one embodiment, a flow assembly for cells comprises a first flow path configured to receive a plurality of cells and having an inner diameter of 50-100 µm, a second flow path configured to receive a buffer and having an inner diameter of 100-200 µm, and a third flow path configured to receive the plurality of cells and the buffer. The third flow path has an inner diameter greater than the inner diameters of the first and second flow paths. The plurality of cells are in a single-file orientation and the buffer generally surrounds the single-file orientation of the plurality of cells when in the third flow path.

In another embodiment, a flow assembly for cells comprises a first flow path configured to receive a plurality of cells, a second flow path configured to receive a buffer, and a third flow path configured to receive the plurality of cells and the buffer. The third flow path has an inner diameter of 0.3-2.0 mm. The plurality of cells are configured to flow in a single-file orientation and the buffer generally surrounds the single-file orientation of the plurality of cells when in the third flow path. At least one of the plurality of cells and the buffer has a flow rate of 25-40 µL/min.

In a further embodiment, a method of characterizing protein structure within a cell comprises providing a first flow path, flowing a plurality of cells through the first flow path, providing a second flow path spaced apart from the first flow path, and flowing a buffer through the second flow path. The method further comprises providing a third flow path with an inner diameter of 0.3-2.0 mm, surrounding the plurality of cells with the buffer, and flowing the plurality of cells in a single-file orientation through the third flow path. The method also comprises emitting a light source through at least a portion of the third flow path, passing the single-file orientation of the plurality of cells through the light source, and identifying a protein structure within each of the plurality of cells.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The foregoing aspects and many of the intended advantages of this invention will become more readily appreciated as the same becomes better understood by reference to the following detailed description when taken in conjunction with the accompanying drawings.

Figure 1:
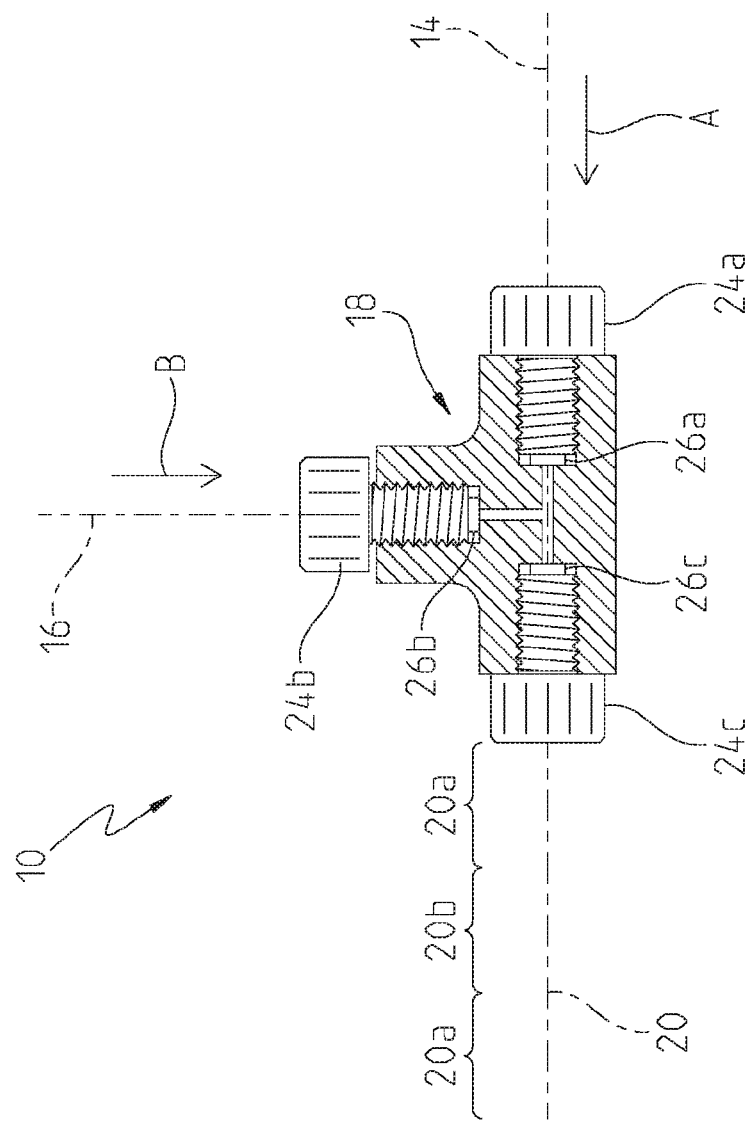
FIG. 1 is a schematic view of a flow system of the present disclosure.

Corresponding reference characters indicate corresponding parts throughout the several views. Although the drawings represent embodiments of various features and components according to the present disclosure, the drawings are not necessarily to scale and certain features may be exaggerated in order to better illustrate and explain the present disclosure. The exemplifications set out herein illustrate embodiments of the invention, and such exemplifications are not to be construed as limiting the scope of the invention in any manner.

DETAILED DESCRIPTION OF THE DRAWINGS

For the purposes of promoting an understanding of the principals of the invention, reference will now be made to the embodiments illustrated in the drawings, which are described below. The embodiments disclosed below are not intended to be exhaustive or limit the invention to the precise form disclosed in the following detailed description. Rather, the embodiments are chosen and described so that others skilled in the art may utilize their teachings. It will be understood that no limitation of the scope of the invention is thereby intended. The invention includes any alterations and further modifications in the illustrative devices and described methods and further applications of the principles of the invention which would normally occur to one skilled in the art to which the invention relates.

Figure 2:
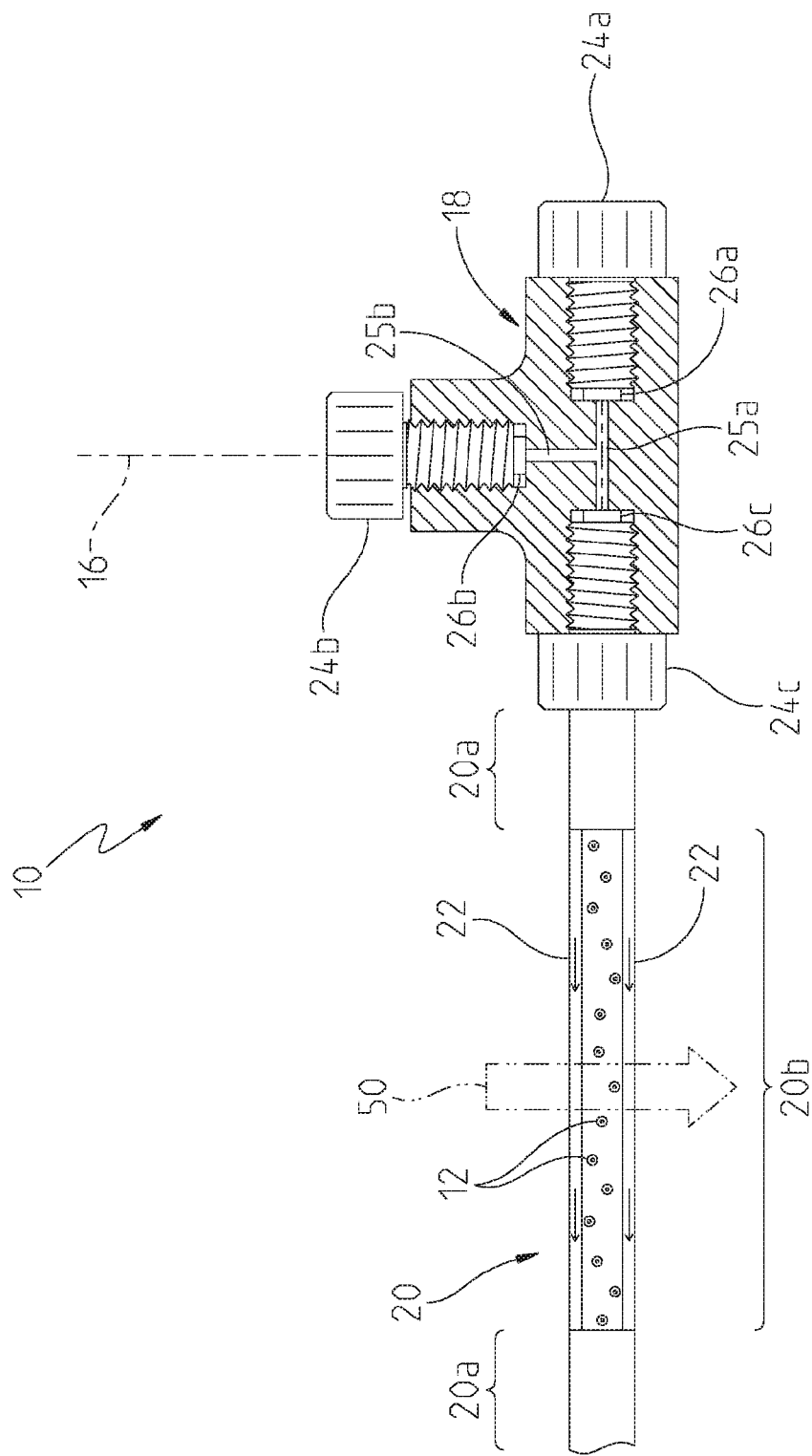
FIG. 2 is a schematic view of a portion of the flow system of FIG. 1.

Referring to FIG. 1, a flow assembly 10 for a plurality of cells 12 (FIG. 2) is provided. Flow assembly 10 includes a first flow path or conduit 14, a second flow path 16 or conduit, a joining member 18, and a third flow path or conduit 20. Flow assembly 10 is configured to move cells 12 through third flow path 20 in a single-file orientation, as shown in FIG. 2 and disclosed further herein.

In the illustrative embodiment of flow assembly 10, first flow path 14 is configured to receive cells 12 and provide a pathway to move cells 12 into joining member 18 along a flow direction A. Cells 12 may be provided within a solution or other material to facilitate flow through flow assembly 10. In one embodiment, cells 12 are provided within a phosphate buffer saline ("PBS") solution and are configured to flow through flow assembly 10 at a flow rate of 25-40 µL/min. More particularly, cells 12 within the PBS material are configured to flow through flow assembly 10 at a flow rate of 33 µL/min.

Cells 12 also may be mixed with an oxygen-based compound, mixture, or solution, such as hydrogen peroxide ($H_2O_2$) for characterizing the proteins within cells. More particularly, cells 12 may be mixed with hydrogen peroxide prior to introducing cells 12 into flow assembly 10 such that the combination of cells 12 and hydrogen peroxide flow together through flow assembly 10. As disclosed further herein, the hydrogen peroxide is photolyzed by a laser or light source to form hydroxyl radicals which covalently label side chains of the amino acids of cells 12 through an in cell fast photochemical oxidation of proteins ("IC-FPOP") process. In this way, the proteins within cells 12 are oxidatively characterized by the hydroxyl radicals when flowing through a portion of flow assembly 10.

First flow path 14 is comprised of any material configured to allow cells 12 to flow therethrough without adhering to the surface of first flow path 14. In one embodiment, first flow path 14 is comprised of fused silica capillary tubing coated with polyimide and/or quartz. Additionally, the length of first flow path 14 may vary to accommodate various configurations of flow assembly 10. An inner diameter of first flow path 14 may be 50 µm, 55 µm, 60 µm, 65 µm, 70 µm, 75 µm, 80 µm, 85 µm, 90 µm, 95 µm, 100 µm, or within any range delimited by any pair of the foregoing values. An outer diameter of first flow path 14 may be 300 µm, 310 µm, 320 µm, 330 µm, 340 µm, 350 µm, 360 µm, 370 µm, 380 µm, 390 µm, 400 µm, or within any range delimited by any pair of the foregoing values. Illustrative first flow path 14 has an inner diameter of 75 µm and an outer diameter of 360 µm.

Referring still to FIG. 1, second flow path 16 is configured to receive a buffer material 22 and flow buffer material 22 into joining member 18 along a flow direction B. Illustratively, flow direction B is generally perpendicular to flow direction A, however the second flow path 16 and flow direction B may be in any orientation relative to first flow path 14 and flow direction A (e.g., parallel, perpendicular, or at any angle). Buffer 22 may be a PBS solution or any solution configured to flow through flow assembly 10 without mixing with cells 12, as disclosed further herein. In one embodiment, the flow rate of buffer 22 through flow assembly 10 is 25-40 µL/min and, more particularly, is 33 µL/min. For example, in one embodiment, the flow rate of buffer 22 may be the same as the flow rate of cells 12.

Second flow path 16 is comprised of any material configured to flow buffer 22. In one embodiment, second flow path 16 is comprised of fused silica capillary tubing coated with polyimide and/or quartz. Additionally, the length of second flow path 16 may vary to accommodate various configurations of flow assembly 10. An inner diameter of second flow path 16 may be greater than the inner diameter of first flow path 14, for example 100 µm, 110 µm, 120 µm, 130 µm, 140 µm, 150 µm, 160 µm, 170 µm, 180 µm, 190 µm, 200 µm or within any range delimited by any pair of the foregoing values. An outer diameter of second flow path 16 may be 300 µm, 310 µm, 320 µm, 330 µm, 340 µm, 350 µm, 360 µm, 370 µm, 380 µm, 390 µm, 400 µm, or within any range delimited by any pair of the foregoing values. Illustrative second flow path 16 has an inner diameter of 150 µm and an outer diameter of 360 µm.

Referring to FIGS. 1 and 2, joining member 18 is a tee assembly comprised of a polymeric material, for example polyether ether ketone ("PEEK"). Illustrative joining member 18 includes a plurality of 1/16-inch tubes 25a, 25b, 1/4-28 flat-bottom nuts 24a, 24b, 24c, each with a sleeve extending therethrough (not shown). Each flat-bottom nut 24a, 24b, 24c has a through-hole with a diameter of 0.5 mm extending longitudinally along the length of nuts 24a, 24b, 24c. Because the diameter of the through-hole of each nut 24a, 24b, 24c is greater than the diameter of first and second flow paths 14, 16, the sleeves are included to control the size of the flow path for buffer 22 and cells 12. In particular, the inner diameter of the sleeves are configured to receive the outer diameter of first and second flow paths 14, 16. A plurality of respective ferrules 26a, 26b, 26c are provided to secure the sleeves to first and second flow paths 14, 16. Ferrules 26a, 26b, 26c may be comprised of the same material as joining member 18 and nuts 24a, 24b, 24c, however, illustrative ferrules 26a, 26b, 26c are comprised of ethylene tetrafluoroethylene ("ETFE"). In one embodiment, the sleeves (not shown) are comprised of fluorinated ethylene propylene ("FEP"). Flat-bottom nuts 24a, 24b, 24c may be comprised of the same material as joining member 18 or may be comprised of a different material. Illustratively, flat-bottom nuts 24a, 24b, 24c are comprised of PEEK.

Additionally, first flow path 14 extends between nuts 24a and 24c and is coupled to the sleeves therein with ferrules 26a and 26c. Alternatively, first flow path 14 may terminate in the sleeve of nut 24a and an additional portion of tubing having the same dimensions and characteristics as first flow path 14 may be provided between nuts 24a and 24c.

Referring still to FIGS. 1 and 2, third flow path 20 is coupled to nut 24c of joining member 18. Third flow path 20 is comprised of any material configured to flow buffer 22 and cells 12. In one embodiment, third flow path 20 is comprised of fused silica capillary tubing coated with polyimide. Alternatively, third flow path 20 may be comprised of a quartz capillary. Additionally, the length of third flow path 20 may vary to accommodate various configurations of flow assembly 10. An inner diameter of third flow path 20 may be as little as 0.3 mm, 0.35 mm, 0.4 mm, 0.45 mm, 0.5 mm, 0.55 mm, 0.6 mm, 0.65 mm, 0.7 mm, 0.75 mm, or as great as 1.0 mm, 1.25 mm, 1.5 mm, 1.75 mm, or 2.0 mm, or within any range delimited by any pair of the foregoing values. An outer diameter of third flow path 20 may be as little as 0.5 mm, 0.55 mm, 0.6 mm, 0.65 mm, 0.7 mm, 0.75 mm, 0.8 mm, 0.85 mm, or as great as 1.0 mm, 1.25 mm, 1.5 mm, 1.75 mm, 2.0 mm, or within any range delimited by any pair of the foregoing values. Illustrative third flow path 20 has an inner diameter of 0.45 mm and an outer diameter of 0.76 mm.

As shown in FIGS. 1 and 2, third flow path 20 includes a coated portion 20a and uncoated portion 20b. Coated portion 20a includes the polyimide or quartz coating, however, the coating has been removed in uncoated portion 20b such that the bare capillary tubing is exposed. As disclosed further herein, by removing a portion of the coating in uncoated portion 20b, an irradiation window is defined so that a laser or other light source can pulse light through third flow path 20 as cells 12 pass therethrough, thereby oxidatively modifying the proteins within cells 12 to understand the structure of the proteins therein.

In operation, cells 12 may be in a PBS solution and are mixed wtih hydrogen peroxide when flowing within first flow path 14 in flow direction A toward joining member 18. Simultaneously, buffer 22 flows within second flow path 16 in flow direction B toward joining member 18. Once at joining member 18, cells 12 flow through nut 24a and buffer 22 flows through nut 24b. Cells 12 continue to flow through first flow path 14 while buffer 22 flows around the outer diameter of first flow path 14. In this way, buffer 22 generally surrounds cells 12 but remains separated from and does not mix with cells 12.

After flowing through nut 24c, buffer 22 and cells 12 simultaneously enter third flow path 20, where, despite exiting first flow path 14, cells still 12 do not mix with buffer 22. Instead, buffer 22 generally defines a chamber surrounding cells 12 such that cells 12 flow through the middle of buffer 22 in a single-file orientation. As shown in FIG. 2, when surrounded by buffer 22, the single-file orientation of cells 12 allows each cell 12 to pass one at a time through a given portion of third flow path 20 such that cells 12 are longitudinally aligned but do not vertically stack on top of each other. Both buffer 22 and cells 12 have the same flow rate, for example 33 µL/min, when flowing through flow assembly 10. The combination of this flow rate and the diameter of third flow path 20 allows cells 12 to flow in the single-file orientation through third flow path 20.

Once in third flow path 20, buffer 22 and cells 12 remain separate from each other and do not mix, as shown in FIG. 2. Additionally, FIG. 2 shows that a laser 50 or other light source is applied to uncoated portion 20b of third flow path 20. Illustratively, laser 50 is pulsed at 248 nm and 18 Hz frequency. Because cells 12 flow through third flow path 20 in a single-file orientation, laser 50 is applied equally to each cell 12. Laser 50 oxidatively modifies the proteins within each cell 12 so that the protein structure of each cell 12 can be identified and understood. More particularly, laser 50 is applied at a wavelength and frequency sufficient to photolyze the hydrogen peroxide mixed with cells 12 to form hydroxyl radicals which covalently label side chains of amino acids within cells 12. In this way, the interaction between the hydrogen peroxide and laser 50 characterize and/or identify the proteins within cells 12 through an IC-FPOP process which allows for analysis of the proteins within cells 12.

After flowing through third flow path 20 and experiencing laser 50, cells 12 and buffer 22 are collected. Cells 12 are separated from buffer 22 and/or any remaining hydrogen peroxide or other compounds, elements, or solutions in a centrifuge and cells 12 subsequently undergo mass spectrometry to identify the peptides (comprised of the covalently-labeled amino acids) of the proteins within cells 12, which allows the protein structure of each cell 12 to be understood. In one embodiment, cells 12 are spliced or otherwise cut into smaller pieces before undergoing mass spectrometry.

Figure 3:
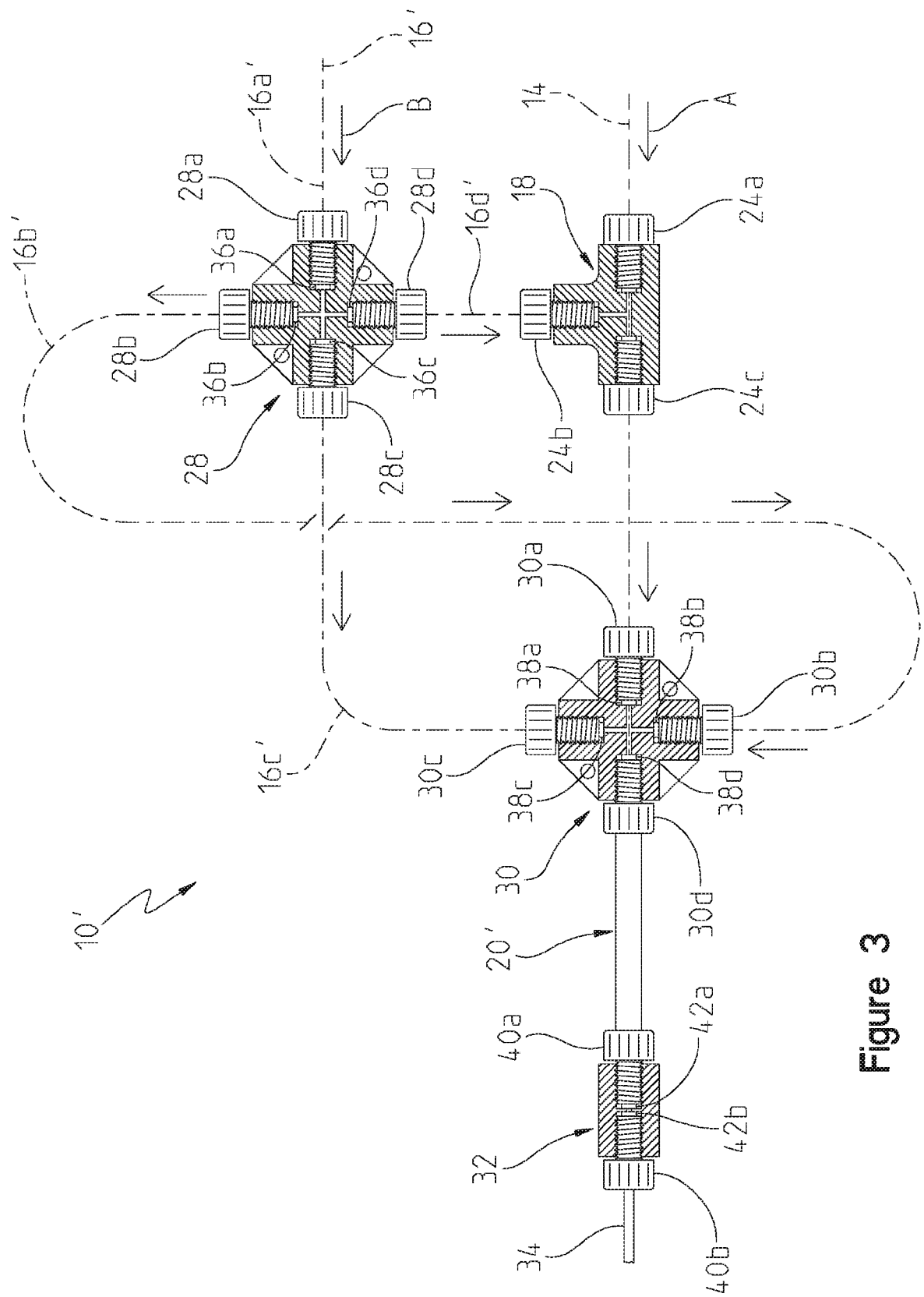
FIG. 3 is a schematic view of an alternative embodiment flow system of the present disclosure.
Figure 4:
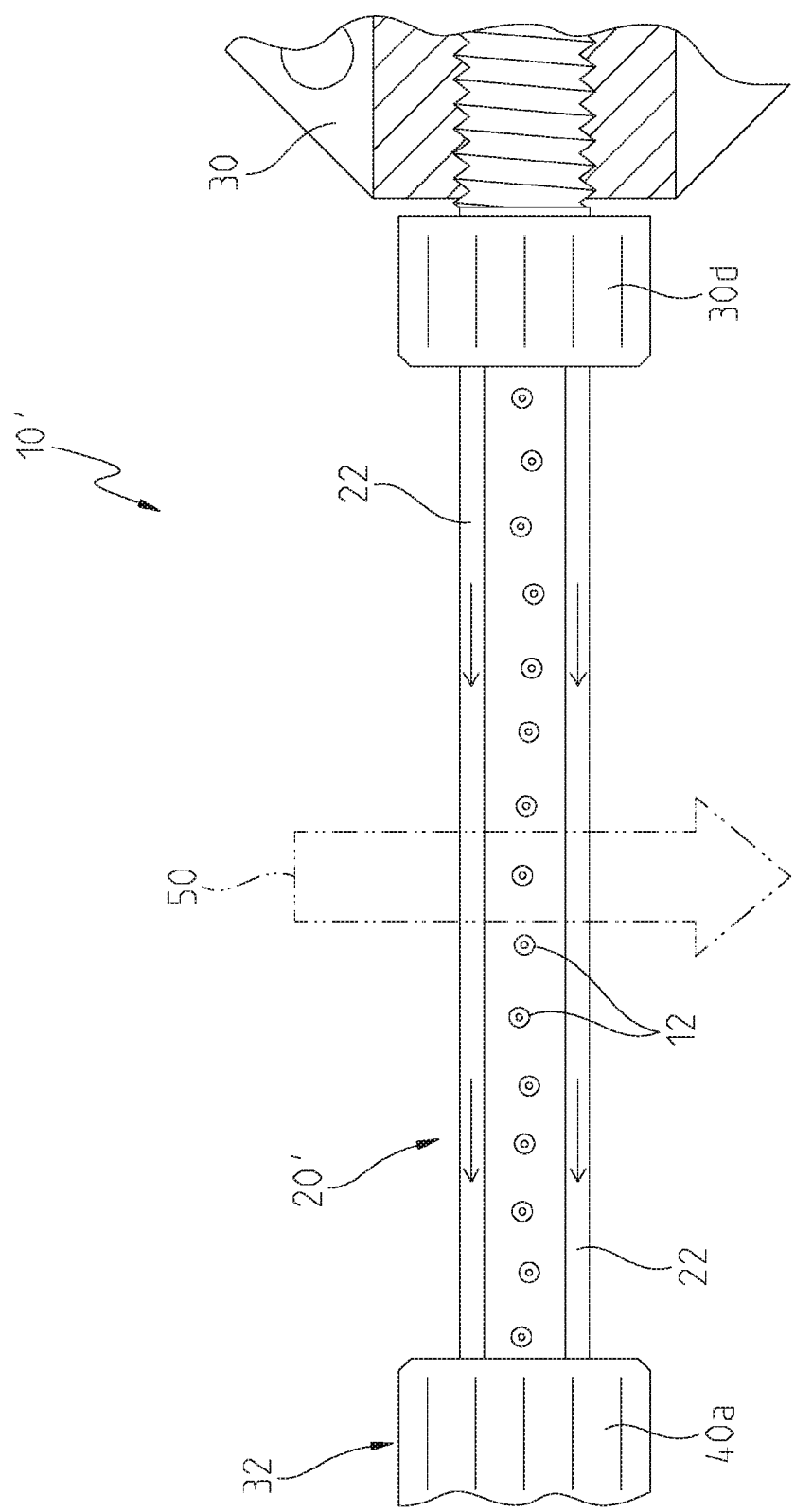
FIG. 4 is a schematic view of a portion of the alternative flow system of FIG. 3.

Referring to FIGS. 3 and 4, an alternative embodiment of flow assembly 10 is shown as flow assembly 10', wherein like components having the same structure and functionality as those of the embodiment of FIGS. 1 and 2 are identified with like reference numbers. Flow assembly 10' includes first flow path 14, a second flow path or conduit 16', joining member 18, and a third flow path or conduit 20'. Additionally, flow assembly 10' includes a first cross-member 28, a second cross-member 30, a dead volume portion 32, and an outlet capillary or conduit 34.

Second flow path 16' is comprised of any material configured to flow buffer 22. In one embodiment, second flow path 16' is comprised of fused silica capillary tubing coated with polyimide and/or quartz. Additionally, the length of second flow path 16' may vary to accommodate various configurations of flow assembly 10'. An inner diameter of second flow path 16' may be 100 µm, 110 µm, 120 µm, 130 µm, 140 µm, 150 µm, 160 µm, 170 µm, 180 µm, 190 µm, or 200 µm or within any range delimited by any pair of the foregoing values. An outer diameter of second flow path 16 may be 300 µm, 310 µm, 320 µm, 330 µm, 340 µm, 350 µm, 360 µm, 370 µm, 380 µm, 390 µm, or 400 µm, or within any range delimited by any pair of the foregoing values. Illustrative second flow path 16' has an inner diameter of 150 µm and an outer diameter of 360 µm.

Second flow path 16' has a first portion 16a' configured to flow a first portion of buffer 22 into first cross-member 28, a second portion 16b' configured to flow a second portion of buffer 22 into second cross-member 30, a third portion 16c' configured to flow a third portion of buffer 22 into second cross-member 30, and a fourth portion 16d' configured to flow a fourth portion of buffer 22 into joining member 18.

As shown in FIG. 3, first cross-member 28 includes four 1/16-inch tubing, 1/4-28 flat bottom nuts 28a, 28b, 28c, 28d, each with a sleeve extending therethrough (not shown). Each flat-bottom nut 28a, 28b, 28c, 28d has a through-hole with a diameter of 0.5 mm extending longitudinally along the length of nuts 28a, 28b, 28c, 28d. Because the diameter of the through-hole of each nut 28a, 28b, 28c, 28d is greater than the diameter of second flow path 16', the sleeves are included to control the size of the flow path for buffer 22. In particular, the inner diameter of the sleeves are configured to receive the outer diameter of second flow path 16'. A plurality of ferrules 36a, 36b, 36c, 36d are provided to secure the sleeves to second flow path 16'. Ferrules 36a, 36b, 36c, 36d may be comprised of ETFE. Flat-bottom nuts 28a, 28b, 28c, 28d may be comprised PEEK.

Referring still to FIG. 3, second cross-member 30 includes four 1/16-inch tubing, 1/4-28 flat bottom nuts 30a, 30b, 30c, 30d, each with a sleeve extending therethrough (not shown). Each flat-bottom nut 30a, 30b, 30c, 30d has a through-hole with a diameter of 0.5 mm extending longitudinally along the length of nuts 30a, 30b, 30c, 30d. Because the diameter of the through-hole of each nut 30a, 30b, 30c, 30d is greater than the diameter of first and second flow paths 14, 16', the sleeves are included to control the size of the flow path for cells 12 and buffer 22. In particular, the inner diameter of the sleeves are configured to receive the outer diameter of first and second flow paths 14, 16'. A plurality of ferrules 38a, 38b, 38c, 38d are provided to secure the sleeves to first and second flow paths 14, 16'. Ferrules 38a, 38b, 38c, 38d may be comprised of ETFE. Flat-bottom nuts 30a, 30b, 30c, 30d may be comprised PEEK.

As shown in FIG. 3, nuts 28b and 30b are fluidly coupled together through second portion 16b' of second flow path 16' such that buffer 22 from first cross-member 28 enters second cross-member 30 through second portion 16b'. Similarly, nuts 28c and 30c are fluidly coupled together through third portion 16c' of second flow path 16' such that buffer 22 from first cross-member 28 enters second cross-member 30 through third portion 16c'. Nut 24c of joining member 18 is fluidly coupled to nut 30a of second cross-member 30 through first flow path 14 and nut 30d of second cross-member 30 is fluidly coupled to third flow path 20'.

Third flow path 20' is comprised of any material configured to flow buffer 22 and cells 12. In one embodiment, third flow path 20' is comprised of a quartz capillary. Additionally, the length of third flow path 20' may vary to accommodate various configurations of flow assembly 10'. An inner diameter of third flow path 20' may be 1.0 mm, 1.1 mm, 1.2 mm, 1.3 mm, 1.4 mm, 1.5 mm, 1.6 mm, 1.7 mm, 1.8 mm, 1.9 mm, 2.0 mm, or within any range delimited by any pair of the foregoing values. An outer diameter of third flow path 20' may be as little as 1.5 mm, 1.6 mm, 1.7 mm, 1.8 mm, 1.9 mm, 2.0 mm, 2.1 mm, 2.2 mm, 2.3 mm, 2.4 mm, 2.5 mm, or within any range delimited by any pair of the foregoing values. Illustrative third flow path 20' has an inner diameter of 1.5 mm and an outer diameter of 1.8 mm.

Dead volume portion 32 is coupled to third flow path 20' and includes two $\frac{1}{16}$-inch tubing, $\frac{1}{4}$-28 flat bottom nuts 40a, 40b. Outlet capillary 34 is configured to be received through nuts 40a, 40b and secured with ferrules 42a, 42b, respectively. As such, outlet capillary 34 is fluidly coupled to third flow path 20' through dead volume portion 32. Outlet capillary 34 is comprised of PEEK and, in one embodiment, has an inner diameter of 0.3 mm and an outer diameter of 1.6 mm. Because the diameter of third flow path 20' is greater than the diameter of outlet capillary 34, dead volume portion 32 is provided to reduce air bubbles in buffer 22 and/or the solution of cells 12 to ensure that there is no delay or break in the flow of cells 12 and/or buffer 22 when going from the larger diameter of third flow path 20' to the smaller diameter of outlet capillary 34.

In operation, cells 12 may be in a PBS solution and mixed with hydrogen peroxide when flowing within first flow path 14 toward joining member 18. Once at joining member 18, cells 12 flow through nuts 24a, 24c and into nut 30a of second cross-member 30. Simultaneously, a portion of buffer 22 flows through nut 28d of first cross-member 28, into nut 24b of joining member 18, around first flow path 14, through nut 24c of joining member 18, and into nut 30a of second cross-member 30. Additionally, a portion of buffer 22 simultaneously flows through nut 28b of first cross-member 28, through second portion 16b' of second flow path 16', and into nut 30b of second cross-member 30. In this way, the portion of buffer 22 within second portion 16b' of second flow path 16' defines the lower portion of the buffer chamber or sheath that generally surrounds cells 12 within third flow path 20'. Additionally, another portion of buffer 22 simultaneously flows through nut 28c of first cross-member 28, through third portion 16c' of second flow path 16', and into nut 30c of second cross-member 30. In this way, the portion of buffer 22 within third portion 16c' of second flow path 16' defines the upper portion of the buffer chamber or sheath that generally surrounds cells 12 within third flow path 20'. The amount of buffer 22 flowing through second and third portions 16b', 16c' of second flow path 16' may be greater than the amount of buffer 22 flowing through fourth portion 16d' and into joining member 18.

Within joining member 18 and second cross-member 30, cells 12 (mixed with hydrogen peroxide) continue to flow through first flow path 14 while buffer 22 flows around the outer diameter of first flow path 14. In this way, buffer 22 generally surrounds cells 12 but does not mix with cells 12. After flowing through nut 30d of second cross-member, buffer 22 and cells 12 simultaneously enter third flow path 20, where, despite exiting first flow path 14, cells 12 do not mix with buffer 22. Instead, buffer 22 generally defines a chamber surrounding cells 12 such that cells 12 flow through the middle of buffer 22 in a single-file orientation. As shown in FIG. 4, when surrounded by buffer 22, the single-file orientation of cells 12 allows each cell 12 to pass one at a time through a given portion of third flow path 20' such that cells 12 are longitudinally aligned but do not vertically stack on top of each other. Both buffer 22 and cells 12 have the same flow rate, for example 33 µL/min, when flowing through flow assembly 10'. The combination of the flow rate and the diameter of third flow path 20' allows for the single file orientation of cells 12 through third flow path 20'.

Once in third flow path 20', buffer 22 and cells 12 (mixed with hydrogen peroxide) remain separate from each other and do not mix, as shown in FIG. 4. Additionally, FIG. 4 shows that laser 50 is applied to a portion of third flow path 20'. Illustratively, laser 50 is pulsed at 248 nm and 18 Hz frequency. Because cells 12 flow through third flow path 20' in a single-file orientation, laser 50 is applied equally to each cell 12.

Laser 50 oxidatively modifies the proteins within each cell 12 through the IC-FPOP process so that the protein structure of each cell 12 can be identified and understood, as disclosed herein. After flowing through third flow path 20' and experiencing laser 50, cells 12 and buffer 22 flow through dead volume portion 32, through outlet capillary 34, and are collected. Cells 12 are separated from buffer 22 and any remaining hydrogen peroxide or other compounds, solution, or elements in a centrifuge and cells 12 subsequently undergo mass spectrometry to identify the peptides of the proteins within cells 12, which allows the protein structure of each cell 12 to be understood. In one embodiment, cells 12 are spliced or otherwise cut into smaller pieces before undergoing mass spectrometry.

Figure 5:
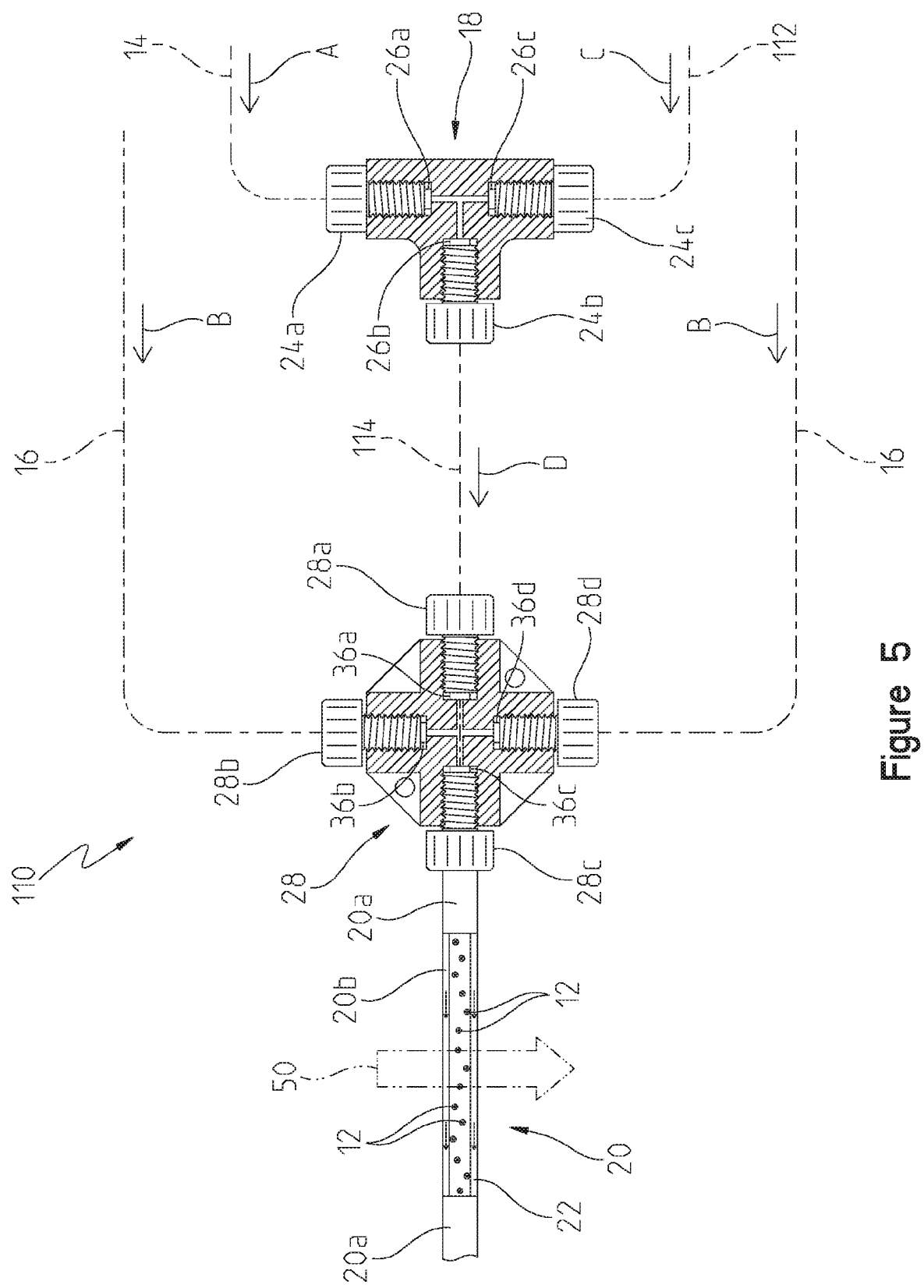
FIG. 5 is a schematic view of an alternative embodiment flow system of the present disclosure.

Referring to FIG. 5, an alternative embodiment of flow assembly 10' (FIG. 3) is shown as flow assembly 110, wherein like components having the same structure and functionality as those of the embodiment of FIGS. 3 and 4 are identified with like reference numbers. Flow assembly 110 includes first flow path 14 (which has the same structure and functionality as flow path 14 of FIG. 3), a second flow path 16 (which has the same structure and functionality as flow path 16 of FIG. 3), a third flow path 112, joining member 18 (which has the same structure and functionality as joining member 18 of FIG. 3), a fourth flow path 114 (which has the same structure and functionality as flow path 14 of FIG. 3), a fifth flow path 20 (which has the same structure and functionality as flow path 20 of FIG. 3), and cross-member 28 (which has the same structure and functionality as cross-member 28 of FIG. 3).

As shown in FIG. 5, joining member 18 is fluidly coupled to first flow path 14 to provide cells 12 to joining member 18 through nut 24a. Additionally, joining member 18 is fluidly coupled to third flow path 112 to provide an oxygen-based solution or compound, such as hydrogen peroxide, to joining member 18 through nut 24c. In this way, cells 12 are separated from hydrogen peroxide until cells 12 and hydrogen peroxide flow to joining member 18. Because hydrogen peroxide may be toxic or damaging to cells 12, flow assembly 110 allows for separation of cells 12 and hydrogen peroxide until both cells 12 and hydrogen peroxide flow to joining member 18, which decreases the length of time that cells 12 are in contact with hydrogen peroxide, thereby decreasing the likelihood that cells 12 may be damaged by hydrogen peroxide. In one embodiment, flow assembly 110 is provided for IC-FPOP processes.

Once cells 12 and hydrogen peroxide are combined at joining member 18, the combination of cells 12 and hydrogen peroxide flow together through fourth flow path 114 toward cross-member 28. Once at cross-member 28, cells 12 (mixed with hydrogen peroxide) flow into cross-member through nut 28a.

Buffer 22 also flows into cross-member 28 through at least one of the second flow paths 16 which are fluidly coupled to nuts 28b, 28d. At cross-member 28, buffer 22 remains separated from cells 12 such that buffer 22 flows in the same direction as cells 12 but flows along the outer circumference of the flow path or conduit of cells 12. In this way, cells 12 do not mix with buffer 22 when at cross-member 28.

In operation, cells 12 may be in a PBS solution (separate from hydrogen peroxide) and flow within first flow path 14 toward joining member 18 in direction A. Simultaneously, hydrogen peroxide flows within third flow path 112 toward joining member 18 in direction C. Once at joining member 18, cells 12 flow through nut 24a and hydrogen peroxide flows through nut 24c such that cells 12 mix with hydrogen peroxide once cells 12 and hydrogen peroxide are both within joining member 18. The mixture of hydrogen peroxide and cells 12 flows in direction D through fourth flow path 114 toward cross-member 28.

Simultaneously, at least a portion of buffer 22 flows through second flow path 16 and nut 28b of cross-member 28 and, in some embodiments, at least another portion of buffer 22 simultaneously flows through second flow path 16 and nut 28d of cross-member 28. In this way, the portion of buffer 22 entering nut 28b of cross-member 28 defines the upper portion of the buffer chamber or sheath that generally surrounds cells 12 within fifth flow path 20 and the portion of buffer 22 entering nut 28d of cross-member 28 defines the lower portion of the buffer chamber or sheath that generally surrounds cells 12 within fifth flow path 20. In this way, buffer 22 generally surrounds cells 12 but does not mix with cells 12.

Buffer 22 and cells 12 simultaneously enter fifth flow path 20, where, despite exiting fourth flow path 114, cells 12 do not mix with buffer 22. Instead, buffer 22 generally defines a chamber surrounding cells 12 such that cells 12 flow through the middle of buffer 22 in a single-file orientation. As shown in FIG. 5, when surrounded by buffer 22, the single-file orientation of cells 12 allows each cell 12 to pass one at a time through a given portion of fifth flow path 20 such that cells 12 are longitudinally aligned but do not vertically stack on top of each other. Both buffer 22 and cells 12 have the same flow rate, for example 33 µL/min, when flowing through flow assembly 110. The combination of the flow rate and the diameter of fifth flow path 20 allows for the single file orientation of cells 12 through fifth flow path 20.

Once in fifth flow path 20, buffer 22 and cells 12 (mixed with hydrogen peroxide) remain separate from each other and do not mix, as shown in FIG. 5. Additionally, FIG. 5 shows that laser 50 is applied to uncoated portion 20b of fifth flow path 20. Illustratively, laser 50 is pulsed at 248 nm and 18 Hz frequency. Because cells 12 flow through fifth flow path 20 in a single-file orientation, laser 50 is applied equally to each cell 12.

Laser 50 oxidatively modifies the proteins within each cell 12 so that the protein structure of each cell 12 can be identified and understood, as disclosed herein. After flowing through fifth flow path 20 and experiencing laser 50, cells 12 are separated from buffer 22 and any remaining hydrogen peroxide or other compounds, solution, or elements in a centrifuge and cells 12 subsequently undergo mass spectrometry to identify the peptides of the proteins within cells 12, which allows the protein structure of each cell 12 to be understood. In one embodiment, cells 12 are spliced or otherwise cut into smaller pieces before undergoing mass spectrometry.

Figure 6:
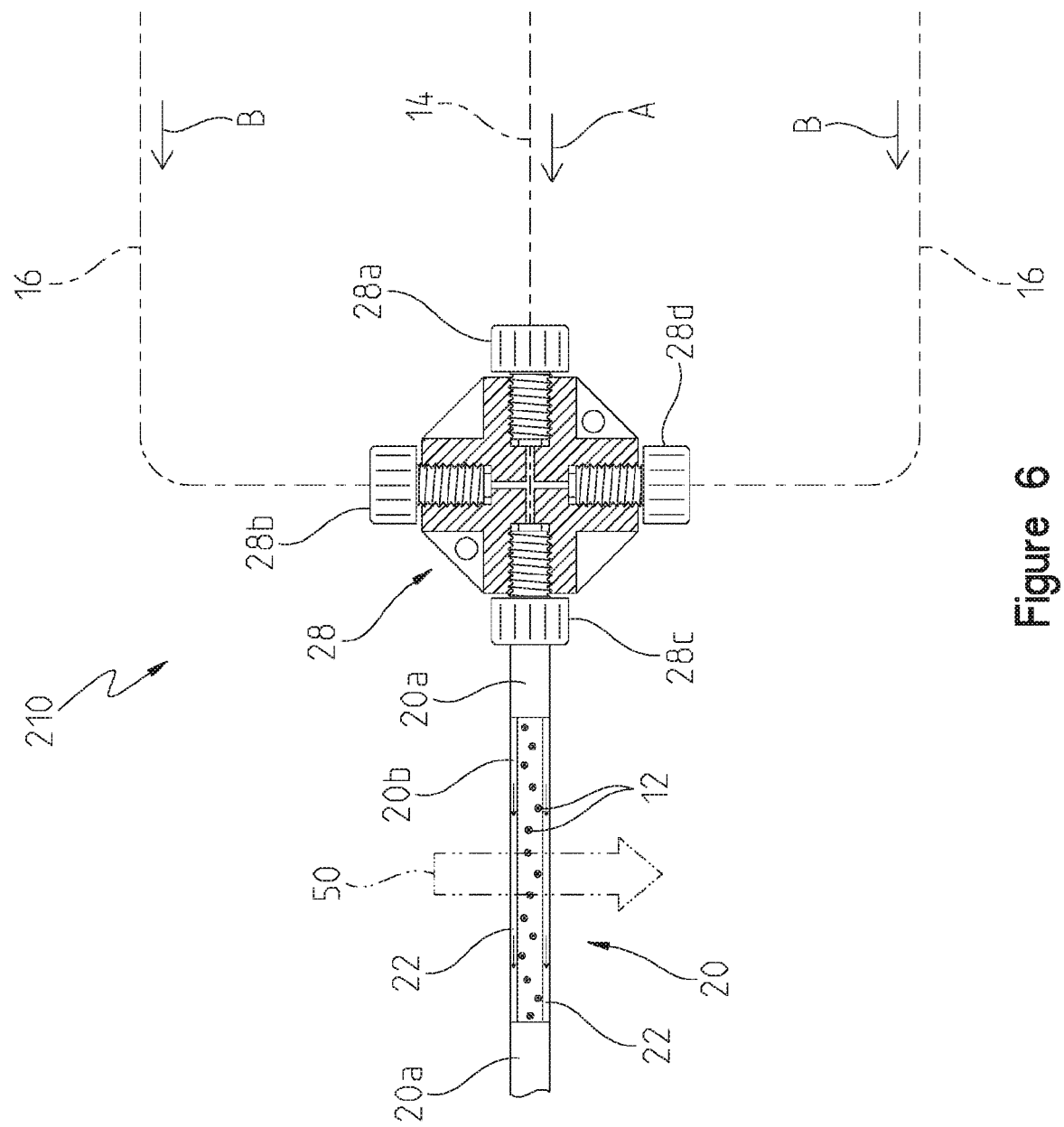
FIG. 6 is a schematic view of a further alternative embodiment flow system of the present disclosure.

Referring to FIG. 6, an alternative embodiment of flow assembly 110 is shown as flow assembly 210, wherein like components having the same structure and functionality as those of the embodiment of FIG. 5 are identified with like reference numbers. Flow assembly 210 includes first flow path 14 (which has the same structure and functionality as flow path 14 of FIG. 5), a second flow path 16 (which has the same structure and functionality as flow path 16 of FIG. 5), a third flow path 20 (which has the same structure and functionality as flow path 20 of FIG. 5), and cross-member 28 (which has the same structure and functionality as cross-member 28 of FIG. 5).

As shown in FIG. 6, joining member 18 of FIG. 5 is removed such that cells 12 are combined with hydrogen peroxide prior to entering first flow path 14. As such, cells 12 flow together with hydrogen peroxide through first flow path 14 toward cross-member 28. Cells 12 and hydrogen peroxide flow into cross-member 28 through nut 28a.

Buffer 22 also flows into cross-member 28 through at least one of the second flow paths 16 (in direction B) which are fluidly coupled to nuts 28b, 28d. At cross-member 28, buffer 22 remains separated from cells 12 such that buffer 22 flows in the same direction as cells 12 but flows along the outer circumference of the flow path or conduit provided for cells 12. In this way, cells 12 do not mix with buffer 22 when at cross-member 28.

In operation, cells 12 (mixed with hydrogen peroxide) may be in a PBS solution and flow within first flow path 14 in direction A toward cross-member 28. Simultaneously, at least a portion of buffer 22 flows through nut 28b of cross-member 28 and, in some embodiments, at least another portion of buffer 22 simultaneously flows through nut 28d of cross-member 28. In this way, the portion of buffer 22 entering nut 28b of cross-member 28 defines the upper portion of the buffer chamber or sheath that generally surrounds cells 12 within third flow path 20 and the portion of buffer 22 entering nut 28d of cross-member 28 defines the lower portion of the buffer chamber or sheath that generally surrounds cells 12 within third flow path 20. In this way, buffer 22 generally surrounds cells 12 but does not mix with cells 12.

Buffer 22 and cells 12 simultaneously enter third flow path 20, where, despite exiting first flow path 14, cells 12 do not mix with buffer 22. Instead, buffer 22 generally defines a chamber surrounding cells 12 such that cells 12 flow through the middle of buffer 22 in a single-file orientation. As shown in FIG. 6, when surrounded by buffer 22, the single-file orientation of cells 12 allows each cell 12 to pass one at a time through a given portion of third flow path 20 such that cells 12 are longitudinally aligned but do not vertically stack on top of each other. Both buffer 22 and cells 12 have the same flow rate, for example 33 µL/min, when flowing through flow assembly 110. The combination of the flow rate and the diameter of third flow path 20 allows for the single file orientation of cells 12 through third flow path 20.

Once in third flow path 20, buffer 22 and cells 12 (mixed with hydrogen peroxide) remain separate from each other and do not mix, as shown in FIG. 6. Additionally, FIG. 6 shows that laser 50 is applied to uncoated portion 20b of third flow path 20. Illustratively, laser 50 is pulsed at 248 nm and 18 Hz frequency. Because cells 12 flow through third flow path 20 in a single-file orientation, laser 50 is applied equally to each cell 12.

Laser 50 oxidatively modifies the proteins within each cell 12 so that the protein structure of each cell 12 can be identified and understood, as disclosed herein. After flowing through third flow path 20 and experiencing laser 50, cells 12 are separated from buffer 22 and any remaining hydrogen peroxide or other compounds, solution, or elements in a centrifuge and cells 12 subsequently undergo mass spectrometry to identify the peptides of the proteins within cells 12, which allows the protein structure of each cell 12 to be understood. In one embodiment, cells 12 are spliced or otherwise cut into smaller pieces before undergoing mass spectrometry.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practices in the art to which this invention pertains.

What is claimed is:

1. A flow assembly for cells, comprising:
    a joining member, the joining member including:
        a cell flow path configured to receive a plurality of cells and having an inner diameter of 50-100 µm; and
        a single buffer flow path configured to receive a buffer and having an inner diameter of 100-200 µm; and
        a third flow path configured to receive the plurality of cells and the buffer and having an inner diameter greater than the inner diameters of the cell flow path and the single buffer flow path throughout an entire length of the third flow path, the plurality of cells being in a single-file orientation with the buffer surrounding the single-file orientation of the plurality of cells when in the third flow path, such that the buffer forms a chamber through which the plurality of cells flow through a middle of the chamber in the single-file orientation.

2. The flow assembly of claim 1, wherein the inner diameter of the cell flow path is 75 µm.

3. The flow assembly of claim 1, wherein the inner diameter of the single buffer flow path is 150 µm.

4. The flow assembly of claim 1, wherein the inner diameter of the third flow path is 0.3-2.0 mm.

5. The flow assembly of claim 1, wherein the buffer is phosphate buffered saline.

* * * * *